（12） United States Patent
Faber et al.

(10) Patent No.: US 8,137,629 B2
(45) Date of Patent: Mar. 20, 2012

(54) AIR FRESHENER POWERED VASE

(75) Inventors: Robert D. Faber, Grand Rapids, MI
(US); David W. Baarman, Fennville, MI
(US); Brad A Zylstra, Irvine, CA (US);
Joshua K. Schwannecke, Grand Rapids,
MI (US); Hai D. Nguyen, Grand Rapids,
MI (US)

(73) Assignee: **Access Business Group International
LLC**, Ada, MI (US)

( * ) Notice: Subject to any disclaimer, the term of this patent is extended or adjusted under 35 U.S.C. 154(b) by 143 days.

(21) Appl. No.: 12/574,853

(22) Filed: Oct. 7, 2009

(65) Prior Publication Data

US 2010/0086448 A1    Apr. 8, 2010

Related U.S. Application Data

(60) Provisional application No. 61/195,450, filed on Oct. 7, 2008.

(51) Int. Cl.
*A61L 9/00* (2006.01)

(52) U.S. Cl. .......................... 422/120; 239/34; 422/125
(58) Field of Classification Search .................. 422/120, 422/125; 239/34
See application file for complete search history.

(56) References Cited

U.S. PATENT DOCUMENTS

| | | | |
|---|---|---|---|
| 4,647,428 A | 3/1987 | Gyulay | |
| 4,816,973 A | 3/1989 | Atalla | |
| 4,829,411 A | 5/1989 | Saba | |
| 4,919,981 A | 4/1990 | Levey | |
| 4,926,293 A | 5/1990 | Saba | |
| 4,931,224 A | 6/1990 | Holzner | |
| 5,147,582 A | 9/1992 | Holzner | |
| 5,353,546 A * | 10/1994 | Bock | 47/66.6 |
| 5,361,522 A | 11/1994 | Green | |
| 5,547,721 A | 8/1996 | Kuo | |
| 5,593,641 A | 1/1997 | Hornberger | |
| 5,624,230 A | 4/1997 | Taylor | |
| 5,776,561 A | 7/1998 | Lindauer | |
| 5,788,931 A | 8/1998 | Munoz Quintana | |
| 5,876,678 A | 3/1999 | Harrell | |
| 5,908,231 A | 6/1999 | Huff | |
| 6,013,524 A | 1/2000 | Friars | |
| 6,099,137 A | 8/2000 | McCormack | |

(Continued)

FOREIGN PATENT DOCUMENTS

CN    1765421 A    5/2006

(Continued)

OTHER PUBLICATIONS

Derwent Abstract for DE 3331871 A1, inventor: May; published: Mar. 1985.*

*Primary Examiner* — Sean E Conley
(74) *Attorney, Agent, or Firm* — Alticor Inc.

(57) ABSTRACT

An air freshener device is provided which includes a portion to display cut flowers or other decorative accents, as well as an optionally-powered portion that contains fragrance and one or more of a variety of fragrance dispersal devices. The air freshener device may include an inductive charging system to allow for the device to be electrically charged and placed remotely from its charging base station relying on on-board electrical power storage. Other power sources such as AC or DC power supplies, batteries, or capacitors may also be used to power the air freshener device.

8 Claims, 3 Drawing Sheets

U.S. PATENT DOCUMENTS

| | | |
|---|---|---|
| 6,315,959 B2 | 11/2001 | Mandish |
| 6,318,876 B1 | 11/2001 | Sigro |
| 6,391,398 B1 | 5/2002 | Pesu |
| 6,413,476 B1 * | 7/2002 | Barnhart ............... 422/124 |
| 6,478,440 B1 | 11/2002 | Jaworski |
| 6,569,387 B1 * | 5/2003 | Furner et al. ............ 422/123 |
| 6,632,405 B2 | 10/2003 | Lua |
| 6,928,235 B2 * | 8/2005 | Pollack ................. 392/380 |
| 7,277,626 B2 | 10/2007 | Pesu |
| 7,318,653 B2 | 1/2008 | Chien |
| 2002/0176704 A1 | 11/2002 | Roe |
| 2005/0079113 A1 | 4/2005 | Selander |
| 2005/0169666 A1 * | 8/2005 | Porchia et al. ........... 399/111 |
| 2005/0185392 A1 | 8/2005 | Walter et al. |
| 2006/0002102 A1 | 1/2006 | Leonard |
| 2006/0186219 A1 | 8/2006 | Kent |
| 2006/0188238 A1 | 8/2006 | Kent |
| 2007/0036673 A1 | 2/2007 | Selander |
| 2007/0076440 A1 | 4/2007 | Chien |
| 2007/0109814 A1 | 5/2007 | Logan |
| 2007/0160809 A1 | 7/2007 | Juron |
| 2009/0072783 A1 * | 3/2009 | Gaspar et al. ............ 320/108 |

FOREIGN PATENT DOCUMENTS

| | | |
|---|---|---|
| DE | 3331871 A1 * | 3/1985 |
| EP | 0269524 A2 | 1/1988 |
| EP | 1281406 A1 | 2/2003 |
| GB | 2421184 | 6/2006 |
| KR | 2001095482 A | 11/2001 |
| WO | 03/083365 | 10/2003 |
| WO | 2006/004901 | 1/2006 |
| WO | 2006/084160 | 8/2006 |
| WO | 2007045832 | 4/2007 |

* cited by examiner

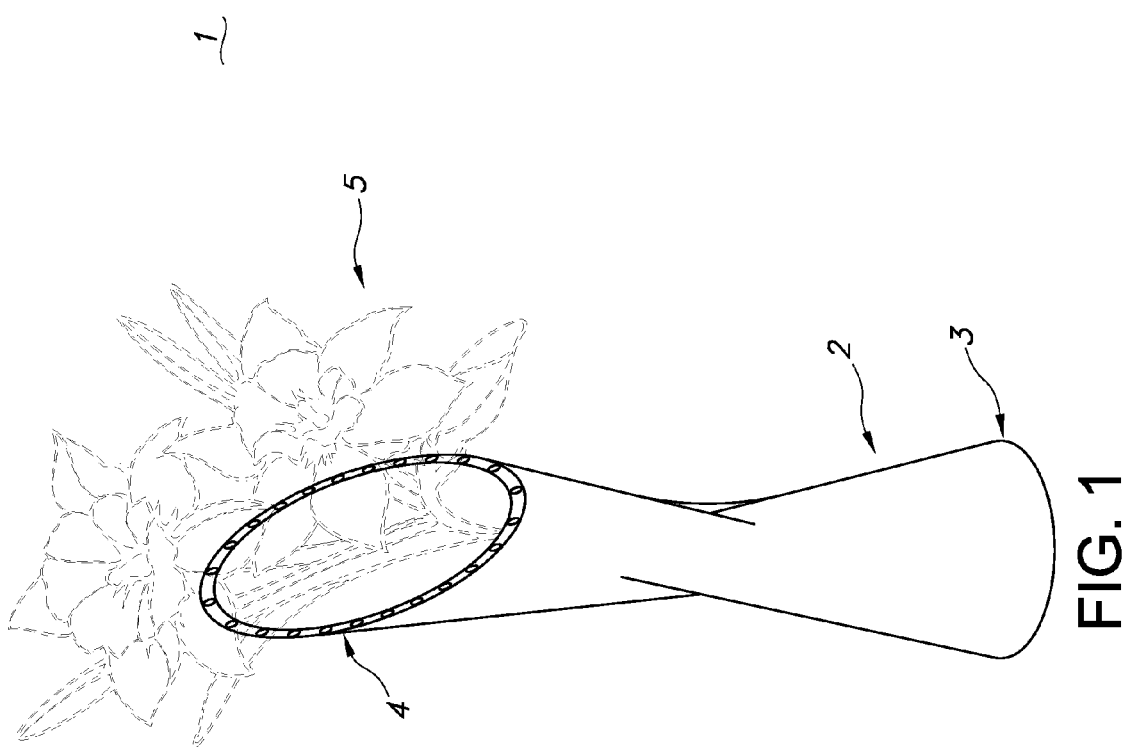

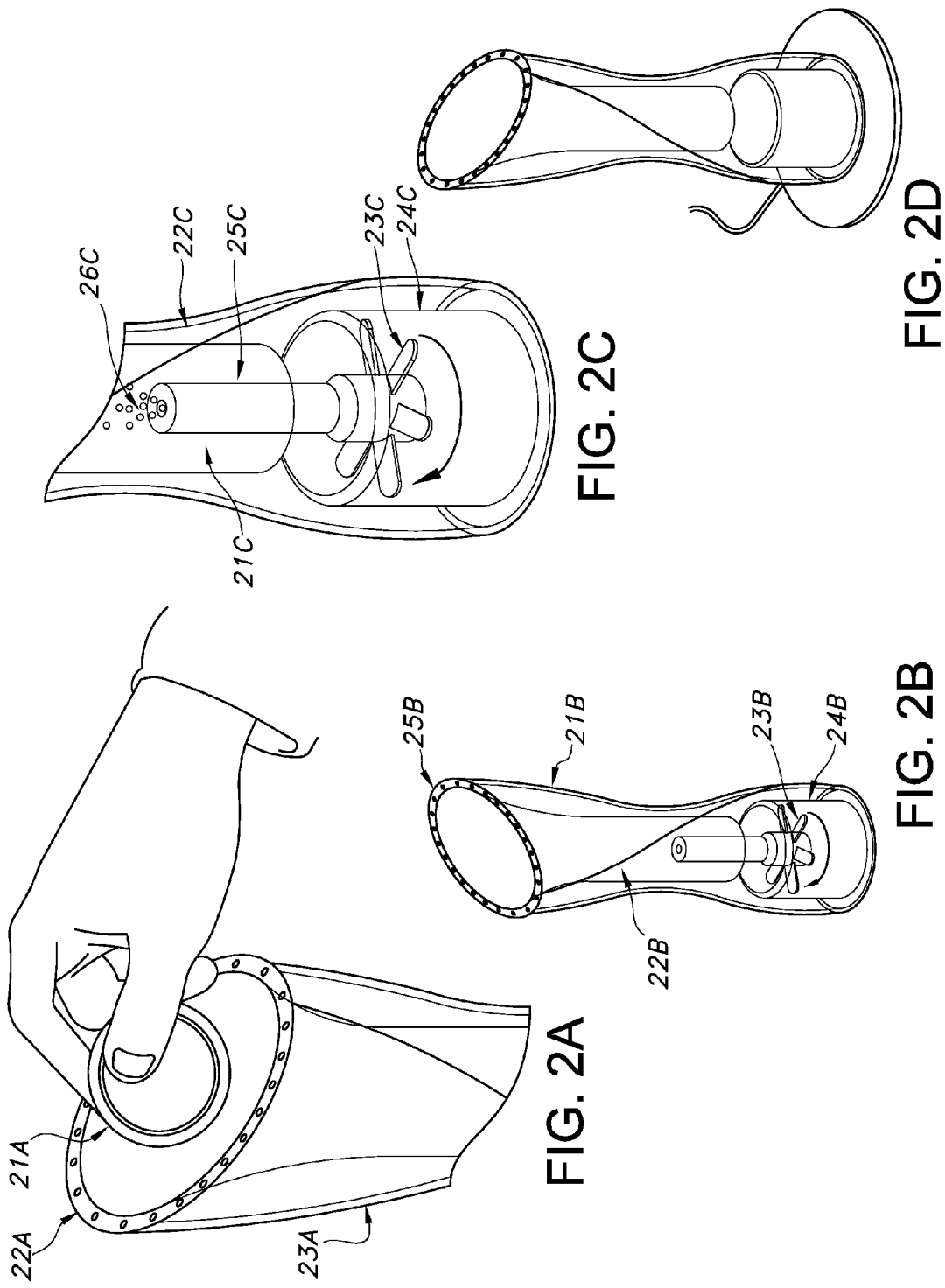

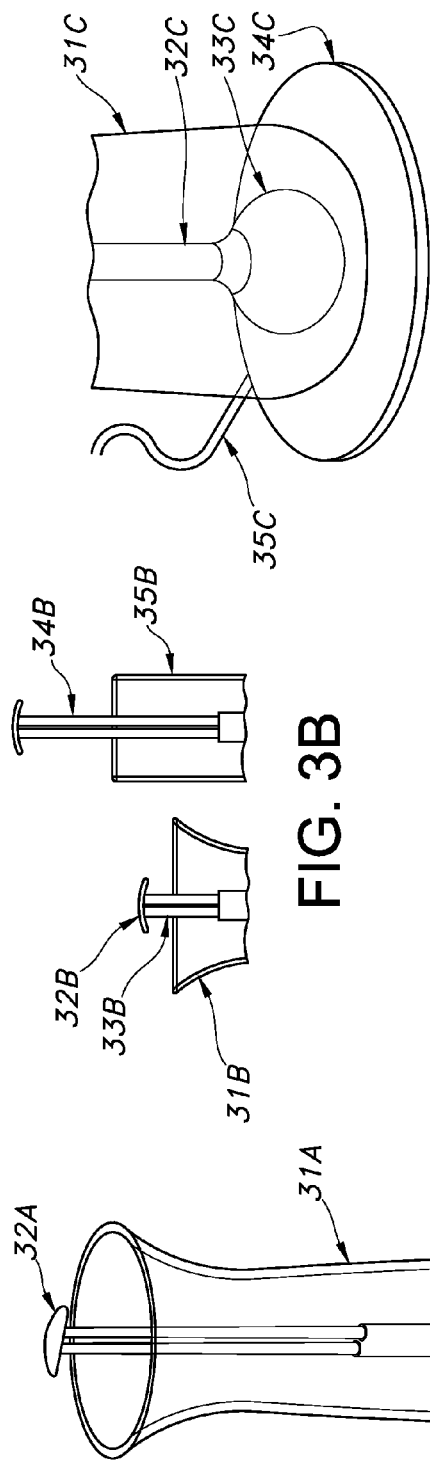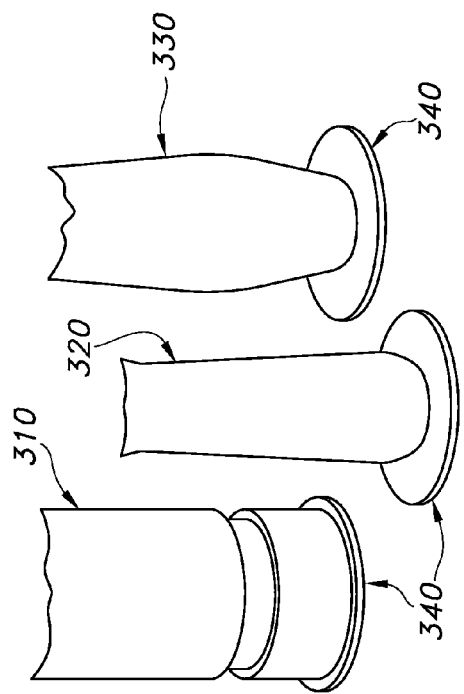

AIR FRESHENER POWERED VASE

This application claims the benefit of U.S. Provisional Patent Application No. 61/195,450 which was filed on Oct. 7, 2008, which is herein incorporated by reference in its entirety.

BACKGROUND OF THE INVENTION

This disclosure relates to air freshening devices and to containers for decorative materials, such as freshly cut flowers, artificial flowers, or other décor.

Air fresheners come in a variety of shapes and sizes. Some are designed to occupy an electrical outlet while holding a fragrance reservoir, with some aid to fragrance dispersal, such as a fan and/or heat, and include a decorative design. Air fresheners such as these have obvious constraints, the primary being that these devices must be used with an electrical outlet, so their level of portability is low. Further, there is no provision for using fresh cut or artificial flowers with this type of air freshener.

Some air fresheners are horizontal units, which are designed to be placed on generally vertical surfaces. These air fresheners may be crafted to accent their surroundings, by resembling pleasing shapes such as sculptures, organic shapes, or geometric shapes.

Other air fresheners are of the wick-type, in that they feature a reservoir for storing a fragrant liquid, into which a wick of some type is inserted. The wick then communicates fragrance through its length, whereupon the local air currents, or assistance by a fan and/or heater distribute the fragrance about an area local to the air freshener. These air fresheners also have some limitations. They do not include a means for displaying flowers, or a fan and/or heater, and the wick method is not very efficient at dispensing fragrance.

Still other air fresheners rely on the vaporization of a fragrance in a reservoir, either a liquid, semi-solid gel, solid, powder, or gas. Some of these air fresheners use a molded fragrance module and rely on exposure to air to cause the volatile fragrance to evaporate into the local environment. Others use an aerosol can connected to a dispensing motor and timer to deliver periodic sprays of fragrance. Still others use a film or membrane impregnated with fragrance, which is transpired to the air. In any of the previous types, there is no provision to display flowers as a part of the air freshener.

SUMMARY OF THE INVENTION

The present invention provides an air freshener device that is in the form of a powered vase or universal vase drop-in insert that enables a user to display flowers and dispense fragrance within an environment. This air freshener device could incorporate a fragrance dispenser, utilizing a fan, heater, or combination of the two to maximize the dispensing of fragrance from within the vase, which also provides a cavity or inner liner for freshly cut flowers, artificial flowers, or other decorative items as the user desires. Further, this air freshener device could be powered from a variety of sources, including AC or DC power, batteries, a rechargeable capacitor, or a wireless power supply, such as inductive coupling technology. An alternative would be a passive air freshener for situations where power assist is not desired.

For a better understanding of the present invention, together with other and further features and advantages thereof, reference is made to the following description, taken in conjunction with the accompanying drawings, and the scope of the disclosure will be laid out in the claims.

It will be readily understood that the components of the present disclosure, as generally described and illustrated in the figures herein, may be arranged and designed in a wide variety of different configurations. Thus, the following more detailed description of the embodiments of the apparatus, system, and method of the present disclosure, as represented in accompanying figures, is not intended to limit the scope of the disclosure, as claimed, but is merely representative of selected embodiments of the disclosure.

Reference throughout this specification to "one embodiment" or "an embodiment" (or similar) means that a particular feature, structure, or characteristic described in connection with the embodiment is included in at least one embodiment of the present disclosure. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. In the following description, numerous specific details are provided, such as examples, to provide a through understanding of embodiments of the present disclosure. One skilled in the art will recognize, however, that the disclosure can be practiced without one or more of the specific details, or with other methods, components, materials, etc. In other instances, well-known structures, materials, or operations are not shown or described in detail to avoid obscuring aspects of the disclosure.

The illustrated embodiments of the disclosure will be best understood by reference to the drawings, wherein like parts are designated by like numerals or other labels throughout. The following description is intended only by way of example, and simply illustrates certain selected embodiments of devices, systems, and processes that are consistent with the disclosure as claimed herein.

DESCRIPTION OF THE DRAWINGS

FIG. 1 is an illustration of one embodiment of the present disclosure. The decorative vase includes the fragrance dispenser while still retaining a reservoir for a water solution when freshly cut flowers are placed in the vase.

FIG. 2A illustrates a scented, nutrient pouch for use in at least one embodiment of the present disclosure.

FIG. 2B is an illustration of the fan/heater element located in the lower portion of the vase, propelling air upward and around the freshly cut, natural flowers, assisting in the dispersal of their natural scent to the environment in one embodiment.

FIG. 2C is an illustration of the fan/heater element with an additional aeration attachment to enhance cut flower life in one embodiment.

FIG. 2D is an illustration of one embodiment, a vase resting on an inductive charging base with primary coil. In this embodiment, an internal battery or capacitor is charged using an inductive coil secondary.

FIG. 3A is an illustration of one embodiment, a vase insert for use with existing vases, and also using an inductive charging base with primary coil to provide a charge to a battery or capacitor within the insert, connected to a secondary coil.

FIG. 3B is an illustration of one embodiment, a vase insert for use with existing vases, including an inductive charging base with primary coil to provide a charge to a battery or capacitor within the insert, connected to a secondary coil. The insert in this embodiment also includes a telescoping feature, which allows for applications where additional height is desired, such as a tall vase.

FIG. 3C is an illustration of one embodiment, a vase insert for use with existing vases, including an inductive charging base with primary coil to provide a charge to a battery or capacitor within the insert, connected to a secondary coil, also including a light source.

FIG. 3D is an illustration of one embodiment, a vase insert for use with existing vases, including an inductive charging base with primary coil to provide a charge to a battery or capacitor within the insert, connected to a secondary coil, using a variety of existing vase shapes and configurations.

DESCRIPTION OF VARIOUS EMBODIMENTS

Referring now to FIG. 1, air freshener vase 1 is shown, and may be of any size or shape of vase suitable for containing flowers or other similar decorative arrangements, such as non-flowering plants, eucalyptus branches, pine boughs, or artificial plants of any type. Vase 1 comprises a decorative outer layer 2, which may be made of a variety of materials, such as plastic resin, composites, glass, crystal, or other suitable material. Within outer layer 2 is powered base 3 (not shown), preferably located in the lower portion of the vase 1, but may be located elsewhere as vase designs dictate. Powered base 3 contains a fan and/or heater element, or a heater element or fan exclusively, to cause fragrance contained with vase 1 to be dispersed in the local environment. Fragrance is added to vase 1 by a variety of mechanisms, including a gel module containing a volatile semi-solid, which is evaporated by increased airflow and/or heat application; a liquid contained in a vessel which is evaporated by the fan and/or heater element within vase 1; a solid which is vaporized by increased airflow by the fan and/or heating by the heater element; or other such fragrance dispersal means such as a powder or spray mist. At the top of vase 1, around the edge defining the interior cavity of the vase, is an array of vent holes 4, which direct airflow from the fan upwards out of the vase, and also allow warm, heated air to escape upward. In both cases, the air exiting vent holes 4 is fragrance-enriched. Additionally, the airflow around the flowers or other naturally fragrant items located within the vase increases the dispersal of the natural fragrance as well as any additional fragrance added within the vase 1.

Referring now to FIG. 2A, pouch 21A is shown being deposited by a user in the opening defined by the vent holes 22A of the inner liner, located at the upper portion of vase 23A. The pouch 21A contains at least one scent or fragrance, and may also include nutrients for use with natural flowers or other cut specimens, such as pine boughs. Although the pouch 21A of the illustrated embodiment is a scented nutrient pouch, the pouch need not include nutrients in all embodiments. The pouch 21A is dropped into the inner liner of vase 23A, whereby liquid, such as water, is added, forming a scented, nutrient solution. Some pouches may contain only nutrients, prepared for specific applications, such as roses, with formulations intended to preserve and extend the life of cut flowers as long as possible. Other pouches may be formulated only for scent or fragrance dispersal, such as for use with artificial flowers, which have no need for nutrients, though a scented, nutrient pouch may be used if desired. If a scent-only pouch is deposited into the vase, the scent may be of a variety of pleasing types, such as jasmine, or be of an odor-masking type designed to eliminate undesirable scents, or odors without injecting a new scent into the environment. These odor-masking pouches may be desirable to users who are sensitive to fragrances and desire a neutral scent environment. Additionally, the number of pouches can be varied for a combination of scents or a single, stronger scent, according to user taste and preference. For purposes of this disclosure, the terms "fragrance" and "scent" are intended to encompass both odor producing and odor masking materials.

FIG. 2B illustrates vase 21B with inner liner 22B, for containing flowers or other décor. Power and control unit 24B is located within vase 21B, at the lower portion, and in this embodiment includes a motor, power supply, control means, and bladed fan 23B. As the fan rotates, air is propelled upward within the vase, and exits the inner liner at the vent holes 25B, which are arrayed around the upper portion of the vase, resulting in the natural fragrance of the fresh flowers held within to be dispersed more widely, and to aid in the dispersal of the evaporating scent solution contained with inner liner 22B. The increased airflow distributes the fragrance more evenly and at a range far greater than the fresh cut flowers alone, and if a scented fragrance pouch (not shown) is used, the level of fragrance broadcasting is even more increased.

FIG. 2C illustrates inner liner 21C within vase 22C, containing a liquid solution. Beneath the inner liner is fan 23C and power and control unit 24C. In this embodiment, the fan propels air upward through the vase 22C, to exit through the vent holes (not shown), but also additionally pumps air into aerator 25C which is connected to the fan and the power and control unit. Air is pumped from those two devices through the aerator into the solution, which causes air bubbles to form and rise through the solution to the surface. The air bubbles aid in fragrance dispersal and may also provide a health benefit to any fresh flowers or other décor contained within the inner liner 21C. The illustrated aerator 25C includes a one-way or "check" valve, to prevent water from flowing back through the fan and power and control unit. Although the illustrated embodiment includes both an aerator and a flow path outside the inner liner, it is not necessary to use them in combination, and either may be used separately from the other, if desired.

FIG. 3A illustrates another embodiment, a drop-in air freshener insert for use with existing vases, additionally with inductive coupling providing electrical power. Vase 31A is shown and in this embodiment, may be a vase of any type, glass, plastic, ceramic or of other suitable material. Drop-in air freshener 32A is shown within vase 31A, including a telescoping tower portion which allows for the upper section to extend beyond the rim of the vase. The telescoping tower portion contains, at its top, an array of vent holes which are connected via air passages to an air pump located at the power base 33A of the air freshener 32A. Within the power base is an air pump, and/or a heating element, a power source, an optional light source, and an air conduit system for pumping air up through the air freshener to the vent holes. The air freshener 32A also includes watertight seals for air connections along the airflow route, which allow for the telescoping action of the upper portion of the air freshener to move relative to the power base, without any loss of air. This is accomplished by an o-ring type seal or other sealing method which allows for the telescoping movement yet prevents air leakage. The power base also includes an inductive coil for receiving power from the base unit 34A, which also houses an inductive coil. By placing the vase 31A with the air freshener 32A inside, on top of base unit 34A, electrical power is inductively transferred from the base unit to the power base within the vase. The power base may also include a capacitor or a battery for storing electrical power for use by the air freshener. Power cord 35A is connected to the base unit 34A, and may be connected to AC power such as found in structures, or DC power, which may be found in vehicles, for example. Additionally, power cord 35A may be attached to a solar cell array for completely pollution-free charging. Although the illustrated embodiment includes an inductive power supply, essentially any wireless power supply technology may be used in alternative embodiments.

Fragrance is added to the drop-in air freshener of this embodiment by separating the telescoping portion from the power base portion. The two portions are joined by a sealable means, such as a threaded or snap fit connection, with a gasket or other water-tight seal to prevent water solution contained in the inner liner from entering the air freshener. The power base portion also contains a fragrance reservoir, beneath which resides the fan and/or heating element, for assisting in evaporating or atomizing the fragrance contained therein. If a fan is used, a water-tight membrane separates the fragrance from the fan, allowing air to flow from the fan through the fragrance and up through the telescoping portion into the environment. There are many membranes which could be used, such as polytetrafluoroethylene (PTFE), which also could be used for the seal between the power base portion and the telescoping tower portion as disclosed above. Although the illustrated embodiment includes a telescoping tower portion, the vase may alternatively include a fixed tower that does not have the ability to telescope. If so, the tower may be configured so that it is relatively hidden by flowers or other items stored in the vase.

FIG. 3B illustrates the adjustability of the drop-in air freshener, for use in a variety of vase shapes and sizes. In this embodiment, the vase 31B is of a short, squat shape, containing flowers 32B. The position of drop-in air freshener 33B, particularly its telescoping portion, is low, with most of the telescoping portion stowed within the air freshener. Thus, the fragrance dispensing portion of the air freshener is high enough to extend beyond the low rim of the vase 31B, but can be well-hidden within the floral arrangement, if desired. In contrast, the telescoping portion of the air freshener 34B is shown in a vase 35B that is tall and narrow, so that the fragrance dispensing portion in this application is extended so that it is exposed above the rim of the taller vase 35B. In this way, the drop-in air freshener is adaptable to a wide variety of vase shapes and sizes, allowing a user to continue using vases already possessed, without the need to discard or acquire additional vases simply to use the drop-in air freshener, if so desired.

FIG. 3C illustrates an embodiment including a light source for use with a drop-in air freshener. Vase 31C, which may, for maximum visual effect, be clear or of a translucent or semi-opaque type, includes a drop-in air freshener 32C, which includes power unit 33C. The power base includes a power source, a pump for propelling air and/or a heating element, and in this embodiment, a light source, such as LEDs or a light bulb. Additionally, the power base includes a power supply and an inductive coil for receiving electrical power from base unit 34C. The power base housing is constructed of a translucent, clear, or semi-opaque material, such as plastic polymer, which allows light to pass from the light source within the power base, through the power base housing, through the liquid solution contained with vase 31C (if any), and through the vase itself, creating a lighting visual effect. The effect can be quite varied, for example, if the drop-in air freshener with light source is used with a crystal vase. Crystal, with its many facets, causes light to reflect and refract in many ways, compared to a standard glass vase. The effect greatly enhances the appeal of the drop-in air freshener when used in this manner. In another example, a colored blown glass vase may be illuminated as well, distributing a tinted light about the environment as well as the fragrance of fresh flowers or décor, and/or a fragrance added through a pouch into the solution contained with the vase. Base unit 34C contains an inductive coil for transferring electrical power through the inductive coil contained within power base 33C, for operation and for charging a power storage device, such as a battery or a capacitor. Power cord 35C is connected to household AC power, DC power, or a solar array for pollution-free operation. Inductive power transfer involves a pair of coils—a primary coil and a secondary coil. Electrical power is supplied to the primary coil, in this embodiment, located in the base unit 34C. Once energized, the primary coil induces a magnetic field in its vicinity. When the power base 33C, with its secondary coil, is placed in this vicinity, power is transferred from the primary to the secondary coil, and is available for use, either to power electronic equipment and/or be stored in a power source, such as a battery, for later use.

FIG. 3D illustrates the drop-in air freshener embodiment when used in a variety of vases of different shapes and sizes. Vases 31D, 32D, and 33D are equipped with drop-in air fresheners powered by inductive coupling base unit 34D. In one application, multiple vases with drop-in air fresheners may be charged by one base unit, or each may have its own base unit for permanent display, or temporary display, depending upon the application desired by the user. The base unit is constructed of materials, such as plastic polymers, to withstand the weight of a vase containing a liquid solution, flowers or décor, and the drop-in air freshener.

If not otherwise stated herein, it is to be assumed that all patents, patent applications, patent publications, and other publications (including web-based publications) mentioned and cited herein are hereby fully incorporated by reference herein as if set forth in their entirety herein.

Although illustrative embodiments of the present disclosure have been described herein with reference to the accompanying drawings, it is to be understood that the disclosure is not limited to those precise embodiments, and that various other changes and modifications may be affected therein by one skilled in the art without departing from the scope or spirit of the disclosure.

The invention claimed is:

1. An air freshener comprising:
   a vase;
   an inner liner disposed within said vase, for containing items;
   a power unit comprising a power supply and at least one of a fan and a heater element;
   a rim joining said vase with said liner, said rim containing a plurality of vent holes;
   a pouch disposed within said liner; and
   an aerator connected to said power unit, for injecting air into said inner liner.

2. The air freshener of claim 1, wherein said pouch contains nutrients for flora.

3. The air freshener of claim 1, wherein said pouch contains a fragrance-releasing medium.

4. The air freshener of claim 1, wherein said pouch contains nutrients and a fragrance-releasing medium.

5. The air freshener of claim 1, further comprising a power supply cord.

6. A drop-in air freshener comprising:
   a power base containing an air pump, a wireless power receiver, and a fragrance reservoir;
   a tower portion engaged with said power base;
   a vent portion disposed near a top of said tower portion, containing a plurality of vents;
   a charging base, which contains an inductive coil and electronic controls; and
   a power cord for supplying power to said charging base.

7. The drop-in air freshener of claim 6, wherein a seal is operatively disposed between said power base and said tower portion.

8. The drop-in air freshener of claim 6, wherein said fragrance reservoir further comprises a membrane allowing air flow in one direction.

\* \* \* \* \*